US00PP19917P2

(12) United States Plant Patent
Bradford

(10) Patent No.: US PP19,917 P2
(45) Date of Patent: Apr. 14, 2009

(54) NECTARINE TREE NAMED 'PEARLICIOUS V'

(50) Latin Name: *Prunus persica*
Varietal Denomination: Pearlicious V

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/003,396

(22) Filed: Dec. 26, 2007

(51) Int. Cl.
*A01H 5/00* (2006.01)

(52) U.S. Cl. ..... Plt./188

(58) Field of Classification Search ..... Plt./188
See application file for complete search history.

(56) References Cited

U.S. PATENT DOCUMENTS

PP16,034 P3 10/2005 Bradford

*Primary Examiner*—Annette H Para
*Assistant Examiner*—June Hwu

(57) ABSTRACT

The present invention relates to a new and distinct variety of nectarine tree, *Prunus persica,* broadly characterized by a small size, vigorous, hardy, self-fertile, productive and regular bearing tree. The variety blooms during the mid season and requires about 525 chilling hours. The fruit matures under the ecological conditions described in late June, with first picking on Jun. 18, 2007. The fruit is medium to large in size, a delicious balance of nectarine flavor with very high sugar, globose in shape, clingstone in type, firm and melting in texture, white in flesh color, and mostly red in skin color.

1 Drawing Sheet

Botanical classification: *Prunus persica.*
Variety denomination: 'Pearlicious V'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Pearlicious V'.

The present variety was hybridized by me in 2001 as a first generation cross using '5P452' (unpatented) nectarine as the selected seed parent and an unnamed low chill nectarine as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2004 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'Spring Pearl' (U.S. Plant Pat. No. 16,034) nectarine by producing nectarines that are firm, mostly red in skin color, white in flesh color, globose in shape, and clingstone in type, but is distinguished therefrom by producing fruit that matures about one week later and that has a blend of traditional nectarine flavor with very high sugar, rather than mildly sub-acidic in taste.

The present variety is similar to its seed parent, '5P452' nectarine, by producing nectarines that are firm in texture, white in flesh color, globose in shape, clingstone in type, and that mature in the latter part of June, but is distinguished therefrom by producing fruit that has more freckling on the skin, that is much sweeter in flavor, and that is more acidic in flavor instead of mildly sub-acidic.

The present variety is similar to its pollen parent, an unnamed low chill nectarine, by producing nectarines that are mostly red in skin color, globose in shape, and clingstone in type, but is distinguished therefrom by having a somewhat higher chilling requirement and by producing fruit that is white in flesh color instead of yellow, that is firmer in texture, and that matures about one week later.

SUMMARY OF VARIETY

In summary, the present variety is characterized by a small size, vigorous, hardy, self-fertile, productive and regular bearing tree. The variety blooms during the mid season and requires about 525 chilling hours. The fruit matures under the ecological conditions described in late June, with first picking on Jun. 18, 2007. The fruit is medium to large in size, a delicious balance of nectarine flavor with very high sugar, globose in shape, clingstone in type, firm and melting in texture, white in flesh color, and mostly red in skin color.

DRAWING

The accompanying photograph consists of four whole fruits positioned to display the characteristics of the skin color and form, one sliced fruit to reveal the flesh, three insets to reveal buds and a blossom, characteristic leaves, a tip shoot, and a typical stone.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 26, 2007, on the original tree during its sixth growing season. The blossom and flower descriptions were made the previous blooming season. All major color code designations are by reference to the Inter-Society Color Council, National Bureau of Standards. Common color names are also used occasionally.

Parentage

Seed parent: '5P452' (unpatented) nectarine.
Pollen parent: Unnamed low chill nectarine.

Tree

Size: Small, reaching and maintaining a height of 7' [2.13 m.] and a spread of 5' [1.52 m.] after six growing seasons utilizing typical dormant pruning.
Vigor: Medium, responding typically to irrigation and fertilization. The variety grows about 2' [0.61 m.] of surplus top-growth during the spring and summer. The plant should be grown on a standard commercial rootstock for production purposes.
Growth: Upright and dense.
Form: Central leader type.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Very productive, thinning necessary.
Fertility: Self-fertile.
Bearing: Regular bearer with no alternate bearing yet observed.
Approximate chilling requirement: 525 hours.
Trunk:
- *Size.*—Slender, reaching a maximum diameter of 2½" [64 mm.] after the sixth growing season.
- *Texture.*—Shaggy.
- *Bark color.*—A Grayish brown [61. gy.Br] and Light grayish brown [60. l.gy.Br] variegation with Deep orange yellow. [69. deep OY] crevices present.
- *Lenticels.*—Approximate Number Per Square Inch: 5. Color: Deep orange yellow [69. deep OY]. Average Size: ¼" [6.4 mm]. Shape: Eye-shaped, elongated.

Branches:
- *Size.*—Diameter of limb is ¾" [19.1 mm.] measured 12" from central leader.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. Older Wood: Deep yellowish brown [75. deep yBr].
- *Lenticels.*—Number Per Square Inch: More than 60 on second year wood. Color: Moderate orange yellow [71. m.OY]. Average size: 1/32" [0.8 mm.] on second year wood. Shape: Rectangular, elongated.

Leaves:
- *Size.*—Medium. Average Length: 6⅛" [156 mm.]. Average Width: 1⅜" [35 mm.].
- *Arrangement.*—Alternate.
- *Thickness.*—Medium.
- *Form.*—Elliptical.
- *Apex.*—Acuminate.
- *Base.*—Acute, with an average base angle of 80 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: 7/16" [11.1 mm.]. Average Thickness: 1/16" [1.6 mm.]. Color: Strong yellow green [117. s.YG].
- *Stipules.*—Number: Usually 2 per leaf, up to 6 per growing tip. Average Length: ¼" [6.4 mm.]. Color: Brilliant yellow green [116. brill.YG] becoming Moderate reddish brown [43. m.rBr] with maturity.
- *Glands.*—Number: 2 to 4 per leaf. Position: Oppositely positioned on petiole and base of blade. Size: Large. Form: Reniform. Color: Brilliant yellow green [116. brill.YG] becoming Moderate reddish brown [43. m.rBr] with age.
- *Leaf buds.*—Pointed, medium in size.

Flower buds:
- *Hardiness.*—Hardy, with respect to central California winters.
- *Diameter.*—Typically ⅜" [9.5 mm.] 1 week before bloom.
- *Length.*—Typically 11/16" [17.5 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, typically thirty or more stamens, five sepal and petal locations alternately positioned.
- *Type.*—Showy, large.
- *Average flower diameter.*—2" [50.8 mm.].
- *Number of petals.*—Some with only five, some with extra petal fragments, more than half are double blossoms with ten petals.
- *Petal shape.*—Circular to oval.
- *Petal margin.*—Entire, somewhat wavy, occasional notches.
- *Average petal diameter.*—13/16" [20.6 mm.].
- *Average petal length.*—⅞" [22.2 mm.].
- *Petal apex.*—Rounded.
- *Petal base.*—Rounded to somewhat truncate.
- *Petal color.*—Pale pink [7. p.Pk] toward the apex, Light purplish pink [249. l.pPk] toward the base on both sides.
- *Anther color.*—Moderate orange [53. m.O] over a Light yellow [86. l.Y] center at bloom onset.
- *Stigma color.*—Pale yellow green [121. p.YG].
- *Sepal color.*—Dark purplish red [259. d.pR] on the outer surface.
- *Sepal length.*—¼" [6.4 mm.].
- *Sepal width.*—3/16" [4.8 mm.].
- *Sepal apex.*—Rounded to elliptical to match the sepal length and width.
- *Sepal margin.*—Fairly smooth.
- *Average pistil length.*—¾" [19.1 mm.].
- *Average stamen length.*—9/16" [14.3 mm.].

*Fragrance.*—Moderate.
*Blooming period.*—Medium, one day before 'Spring Bright' (U.S. Plant Pat. No. 7,507) nectarine.
*Onset of bloom.*—One percent on Mar. 1, 2007.
*Date of full bloom.*—Mar. 8, 2007.
*Duration of bloom.*—One to two weeks, dependent on ambient temperature.
*Number per cluster.*—1 to 3 with single flowers most common.

FRUIT

Maturity when described: Firm ripe, Jun. 26, 2007.
Date of first picking: Jun. 18, 2007.
Date of last picking: Jun. 28, 2007.
Size: Medium to large.
*Average diameter axially.*—2 13/16" [71.5 mm.].
*Average diameter across suture plane.*—2¾" [69.9 mm.].
*Average diameter across cheek plane.*—2¾" [69.9 mm.].
*Typical weight.*—7.8 ounces [221 grams].
Form: Globose, slightly asymmetrical.
*Longitudinal section form.*—Round.
*Axial view.*—Round.
Suture: Extends from the base, along the side, and just past the pistil point.
*Near the base.*—A shallow sharp groove.
*Along the side.*—A shallow trough.
*Near the apex.*—A shallow groove.
Ventral surface: Rounded slightly, lipped toward the apex.
Lips: Slightly unequal.
Cavity: Flaring, circular, suture showing on one side, Yellowish white [92. yWhite] stem markings typical.
*Depth.*—½" [12.7 mm.].
*Breadth.*—1 1/16" [27.0 mm.].
Base: Rounded to slightly truncate.
Apex: Rounded, but somewhat cordate if viewed parallel to the suture.
Pistil point: Apical, very short, usually depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed.
*Color.*—Very deep red [14. v.deep R] smoothly blending into Moderate red [15. m.R] over a Yellowish white [92. yWhite] background with Pale yellow [89. p.Y] freckling toward the apex.
Flesh:
*Color.*—Yellowish white [92. yWhite] with moderate Very red [11. v.R] streaking toward the stone.
*Surface of pit cavity.*—Covered with Very red [11. v.R] broken fibers when twisted from the stone.
*Amygdalin.*—Scant.
*Juice.*—Moderate, rich.
*Texture.*—Firm, crisp.
*Fibers.*—Abundant, fine, tender.
*Ripens.*—Earlier at the apex.
*Flavor.*—A tasty blend of high sugar with a slight amount of traditional nectarine flavor, typically 22 brix.
*Aroma.*—Moderate.
*Eating quality.*—Excellent.

STONE

Type: Clingstone.
Form: Oval.
Hilum: Broad, oval.
Base: Rounded to acute.
Apex: Acute to acuminate.
Sides: Equal.
Surface: Horizontally furrowed toward the apex, pitted toward the base.
Ridges: Somewhat jagged.
External color: Moderate yellowish brown [77. m.yBr].
Pit wall color when cracked: Strong yellowish brown [74. s.yBr].
Cavity surface color: Deep yellowish brown [75. deep yBr].
Average pit wall thickness: ¼" [6.4 mm.].
Average width: 15/16" [23.8 mm.].
Average length: 1¼" [31.8 mm.].
Average breadth: ⅞" [22.2 mm.].
Tendency to split: None observed.
Kernel:
*Form.*—Oval.
*Skin color.*—Dark orange yellow [72. d.OY] when dry.
*Pellicle color.*—Deep yellowish brown [75. Deep y.Br].
*Vein color.*—Strong yellowish brown [74. s.yBr].
*Taste.*—Bitter.
*Viable.*—Yes.
*Average width.*—7/16" [11.1 mm.].
*Average length.*—1 1/16" [17.5 mm.].
*Amygdalin.*—Abundant.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is similar to 'Spring Pearl' (U.S. Plant Pat. No. 16,034) nectarine by producing nectarines that are firm, mostly red in skin color, white in flesh color, globose in shape, and clingstone in type, but is distinguished therefrom by producing fruit that matures about one week later and that has a blend of traditional nectarine flavor with very high sugar, rather than mildly subacidic in taste.

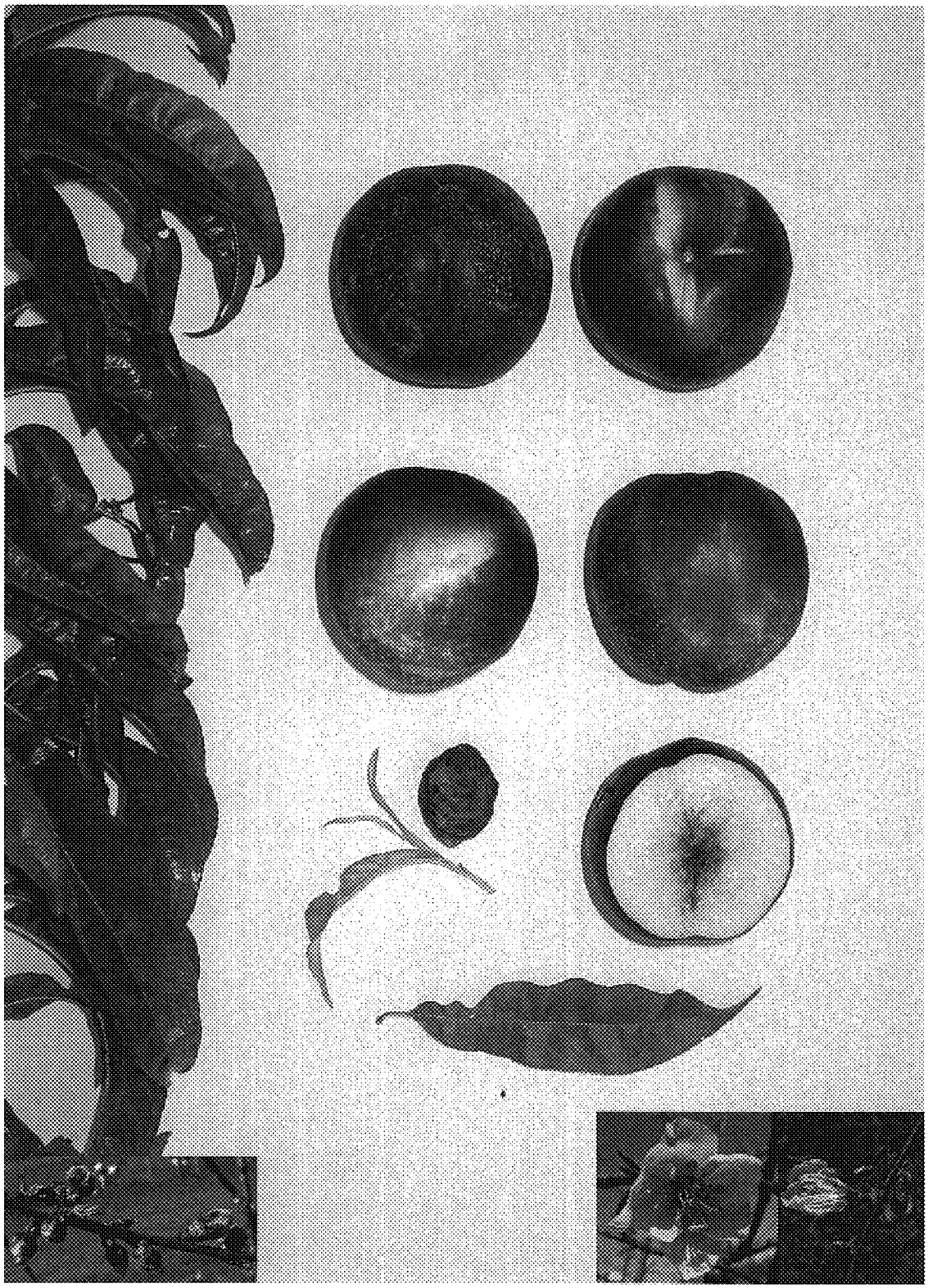

* * * * *